United States Patent
Flanner et al.

(10) Patent No.: US 6,838,093 B2
(45) Date of Patent: Jan. 4, 2005

(54) SYSTEM FOR OSMOTIC DELIVERY OF PHARMACEUTICALLY ACTIVE AGENTS

(75) Inventors: Henry H. Flanner, Montgomery Village, MD (US); Lisa C. McKnight, Fairfax, VA (US); Beth A. Burnside, Bethesda, MD (US)

(73) Assignee: Shire Laboratories, Inc., Rockville, MD (US)

( * ) Notice: Subject to any disclaimer, the term of this patent is extended or adjusted under 35 U.S.C. 154(b) by 0 days.

(21) Appl. No.: 09/872,173

(22) Filed: Jun. 1, 2001

(65) Prior Publication Data

US 2003/0003150 A1 Jan. 2, 2003

(51) Int. Cl.$^7$ .............................. A61K 9/24; A61K 9/20; A61K 9/22; A61K 9/28; A61K 9/14
(52) U.S. Cl. ........................ 424/472; 424/464; 424/465; 424/468; 424/471; 424/473; 424/474; 424/484; 514/960; 514/964
(58) Field of Search ................................. 424/400, 464, 424/465, 468, 471, 472, 473, 474, 480, 484, 479, 482, 475; 514/960, 964

(56) References Cited

U.S. PATENT DOCUMENTS

| | | | |
|---|---|---|---|
| 4,662,880 A | 5/1987 | Hamel et al. ............... 604/892 |
| 4,801,461 A | 1/1989 | Hamel et al. ............... 424/467 |
| 5,681,584 A | * 10/1997 | Savastano et al. .......... 424/473 |
| 5,783,212 A | * 7/1998 | Fassihi et al. .............. 424/472 |
| 6,004,582 A | * 12/1999 | Faour et al. ................ 424/473 |
| 6,051,585 A | * 4/2000 | Weinstein et al. .......... 514/335 |
| 6,248,359 B1 | * 6/2001 | Faour .......................... 424/469 |
| 6,491,949 B2 | * 12/2002 | Faour et al. ................ 424/473 |

\* cited by examiner

*Primary Examiner*—Gary Kunz
*Assistant Examiner*—Sharmila S Gollamudi
(74) *Attorney, Agent, or Firm*—M. Elisa Lane

(57) ABSTRACT

An osmotic system for delivering a pharmaceutically active agent which comprises a core portion, a layer portion enclosing the core portion, and a semipermeable wall portion enclosing the core portion and the layer portion. The core portion includes the pharmaceutically active agent at a first concentration. The pharmaceutically active agent is present in the layer portion at a second concentration. The second concentration is greater than the first concentration. Such a system provides for the osmotic release of the pharmaceutically active agent in release profile other than a zero order release profile, and wherein the release profile is similar to or approaches or reaches a first order release profile.

20 Claims, 1 Drawing Sheet

SYSTEM FOR OSMOTIC DELIVERY OF PHARMACEUTICALLY ACTIVE AGENTS

FIELD OF THE INVENTION

This invention relates to a system for delivering a pharmaceutically active agent. More particularly, this invention relates to a system for delivering a pharmaceutically active agent in which the pharmaceutically active agent is released osmotically in a release profile that approaches or reaches first order. Such a system includes a core portion and a layer portion, wherein the pharmaceutically active agent is present in the layer portion in a greater concentration than in the core portion. A semipermeable membrane surrounds the layer portion and the core portion.

BACKGROUND OF THE INVENTION

Various examples of osmotic drug delivery systems, in the form of tablets, for example, are known. In one example, a semipermeable membrane surrounds a core portion which includes a pharmaceutically active agent. In such systems, the pharmaceutically active agent is released at a constant rate, i.e., a zero order release profile.

In another example, a semipermeable membrane surrounds a core portion which includes a pharmaceutically active agent. An example of such a system is disclosed in U.S. Pat. No. 4,801,461. A layer of the pharmaceutically active agent is on the exterior of the semipermeable membrane. In such systems, the pharmaceutically active agent which is exterior to the semipermeable membrane is released quickly, and in general provides a quick and initial relief of symptoms to a patient. This initial release of the pharmaceutically active agent is at a first constant rate, i.e., a first rapid zero order release profile, also known as an immediate release. After the release of the pharmaceutically active agent which is exterior to the semipermeable membrane, the pharmaceutically active agent in the core portion is released at a second constant ratio, i.e., a second zero order release profile. Although this system may provide an initial quick release of the pharmaceutically active agent, in some cases there may be an excess initial release of the pharmaceutically active agent, or "dose dumping," which is undesirable. Also, in some cases, the pharmaceutically active agent which is on the exterior of the semipermeable membrane may be degraded prematurely by saliva, hydrochloric acid, or other digestive juices and gastric juices.

SUMMARY OF THE INVENTION

It is an object of the present invention to provide a system which provides for a gradual yet effective release of a pharmaceutically active agent, in which there is improved control of release of the drug into the patient, and the pharmaceutically active agent or drug is protected adequately from the environment external to the pharmaceutically active agent or drug.

DETAILED DESCRIPTION OF THE INVENTION

Figure 1:
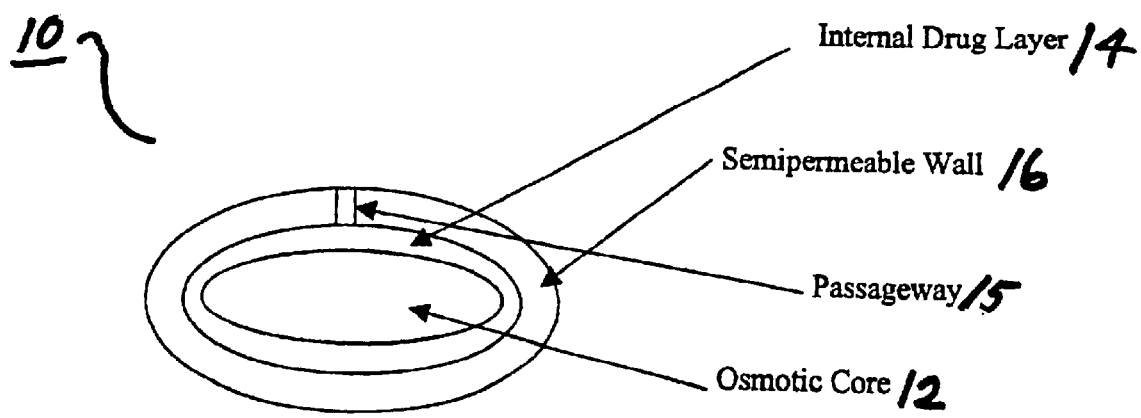
FIG. 1 is a depiction of a tablet according to the present invention.

In accordance with an aspect of the present invention, there is provided an osmotic system for delivering a pharmaceutically active agent. The system comprises a core portion, a layer portion enclosing or surrounding the core portion, and a semipermeable wall portion enclosing or surrounding the core portion and the layer portion. The core portion includes the pharmaceutically active agent at a first concentration, and the layer portion includes the pharmaceutically active agent at a second concentration. The second concentration is greater than the first concentration.

In one embodiment, the pharmaceutically active agent is present in the core portion in an amount of from about 1 wt. % to about 80 wt. %, preferably from about 25 wt. % to about 70 wt. %, more preferably at about 60 wt. %, of the core portion. Also present in the core may be osmagents, flow aids, fillers, and lubricants. The osmagents are included in the core to assist the release of the pharmaceutical agent, especially if it exhibits a low solution osmolality. Examples of osmagents include sodium chloride, xylitol, fructose, sucrose, citric acid and other soluble compounds which exhibit an osmotic pressure gradient across a semipermeable membrane. Flow aids may be added to the formulation to increase the flowability of the pharmaceutical agent and optional core ingredients. Colloidal silicon dioxide and magnesium stearate are commonly used flow aids. Fillers can also be used to add bulk to the pharmaceutical agent to allow for easier processing into a tablet dosage form. Fillers suitable for use in the present invention are soluble in water or physiological fluids or of a fine particle size so as not to block the passageway out of the device. Examples of acceptable fillers include, but are not limited to, lactose, lactitol, pregelatinized starch and so forth. Lubricants are also added to the core to aid release of the tablet from the tablet press die and punches. Acceptable lubricants are those that do not interfere with dissolution of the core tablet or adhesion of the layer portion to the core portion. Lubricants suitable for the present invention include, but are not limited to, magnesium stearate, sodium stearyl fumarate, sodium lauryl sulfate, glyceryl behenate and the like.

In another embodiment, the pharmaceutically active agent is present in the layer portion in an amount of from about 20 wt. % to about 99 wt. %, preferably from about 50 wt. % to about 95 wt. %, more preferably at about 90 wt. %, of the layer portion. Also optionally present in the layer portion are binding agents, plasticizers, and antitacking agents. The binding agent preferably also is a film former capable of binding the pharmaceutical agent of the second layer to the core with good adhesion and a smooth film. The binder should be soluble in water or physiological fluids and should be of sufficiently low viscosity so as not to retard the release of the pharmaceutical agent from the second layer. Preferred binders, include, but are not limited to, low viscosity HPMC (hydroxypropylmethyl cellulose), low viscosity HPC (hydroxypropyl cellulose), Eudragit E polymers (aminoalkyl methacrylate copolymers), Eudragit RD 100 (a mixture of ammonioalkyl methacrylate copolymers and sodium carboxymethylcellulose), PVP K30 (polyvinylpyrrolidone) and the like. Optionally plasticizers and antitacking agents may be added to the layer portion to improve the quality of the film. Acceptable plasticizers include, but are not limited to, PG (Propylene Glycol), TEC (triethyl citrate), Polysorbate 80, dibutyl phthalate etc. Antitacking agent examples include, but are not limited to, talc, magnesium stearate, glyceryl monostearate, titanium dioxide and the like. Additionally commercially available products such as Opadry®, Opagloss®, and Lustre Clear® and others which are ready made mixes of binder, plasticizer and antitacking agents may be used.

The pharmaceutically active agent may be soluble or insoluble. When the pharmaceutically active agent is one that is insoluble, the core portion and the layer portion may include solubilizing agents. Examples of such solubilizing agents include, but are not limited to, (i) agents that inhibit crystal formation of the pharmaceutically active agent or otherwise act by complexation therewith; (ii) high HLB (hydrophilic-lipophilic balance) micelle-forming surfactants, particularly anionic surfactants; (iii) citrate esters; and combinations thereof, particularly combinations of complexation agents with anionic surfactants. Examples of solubilizing agents also are described in U.S. Pat. No. 6,110,498, the contents of which are incorporated herein by reference.

The delivery system is suited ideally to deliver therapeutic agents requiring protection from chemical, biological or enzymatic degradation in the GI tract, as the therapeutic agent is contained wholly within the semipermeable film until released from the tablet. This mode of release from an osmotic delivery device may increase the amount of therapeutic agent absorbed, and may reduce first pass hepatic metabolism by saturating the enzymes in the liver with the faster and earlier rate of release from the present invention. Such therapeutic agents include peptides, proteins and other molecules subject to degradation by chymotrypsin, trypsin, pepsin, and cytochrome 3A4 and other digestive enzymes as well as those subject to degradation by cytochrome P450 or other liver enzymes. Examples include, but are not limited to, cyclosporin, carmustine, carbamazepine, desmopreson, dihydroergotamine, fluorouracil, heparin sodium, ribavirin, sumitriptan succinate, flutamide, naltrexone HCl, terbutaline sulfate, triamterene, calcitonin, insulin, parathyroid hormone, and GLP-1.

Another advantage of the present invention is the ability to deliver therapeutic agent from an osmotic delivery device at a delivery rate that is other than zero order so as to provide faster relief of certain conditions and symptoms. Therapeutic agents which benefit from a faster and earlier release rate than that provided by the prior art osmotic delivery devices are antisussives, antihistamines, expectorants and decongestants. Some examples are chlorpheneramine and its salts, dyphenhydramine, dimenhydramine, pseudoephedrine and its salts, and other similar agents.

Still another advantage of the present invention is the ability of the osmotic delivery device to release the drug at a controlled rate high enough to achieve therapeutic levels in the first few hours of administration without the need of an exterior immediate release coating to provide a "burst" effect. Certain therapeutic agents, particularly the hypertensive agents and especially the direct acting vasodilators can have serious side effects if a high dose of the agent is absorbed too quickly from an immediate release device or layer. The present invention minimizes this effect by providing a controlled delivery of the agent through the passageway. In the present invention, the agent is gradually released and metered out of the device so as to provide the requisite therapeutic benefit without the need for an immediate release or "burst" layer. Therapeutic agents in this category include, but are not limited to, terazosin, parazosin, and nifedipine.

The semipermeable wall or membrane may be formed from any insoluble polymer. In general, the semipermeable wall is composed of a polymeric material cast or sprayed onto the tablet to give a 2 to 15% coating weight. One example of a polymeric material includes, but is not limited to, cellulose acetate. The use of such polymeric material requires plasticizers for increased flexibility, durability, and stability. In the case of cellulose acetate, examples of suitable plasticizers are triethyl citrate (TEC), propylene glycol (PG), a mixture of TEC and PG in ratios ranging from 25% TEC plus 75% PG to 75% TEC plus 25% PG, Tween 80 or other polyoxyethylene sorbitan esters, triacetin, diethyl phthalate, polyethylene glycol, mineral oil, tributyl sebacate, and glycerol. The plasticizers are included as a weight ratio of cellulose acetate suitable for creating a semipermeable wall to achieve retainment of the bioactive substance while permitting water permeation to the layer portion and the core.

The semi-permeable wall can contain at least one passageway communicating the contents of the core and the layer with the exterior of the device, delivering the beneficial drug through the passageways from the elementary osmotic device. The size of an individual passageway can range from 100 microns to 1000 microns, more preferred 300 to 900 microns, most preferred 500 to 850 microns. One or multiple passageways can be present to communicate the contents with the exterior.

Other semipermeable polymers which can be added are cellulose acetate butyrate, ethylcellulose, and any polymer known for use in reverse osmosis or as an osmotic membrane. The semipermeable wall or membrane is insoluble and non-eroding in bodily fluids.

In another embodiment, a first pharmaceutically active agent is included in the core portion, and in the layer portion as hereinabove described, and a second pharmaceutically active agent is placed on the exterior of the semipermeable wall portion. Thus, a core portion and a first layer portion, each of which include the first pharmaceutically active agent, are enclosed or surrounded by the semipermeable wall portion, and a second layer portion, which includes the second pharmaceutically active agent, encloses or surrounds the semipermeable wall portion. Such an embodiment provides for an immediate or quick release of the second pharmaceutically active agent, and a more controlled yet effective osmotic release of the first pharmaceutically active agent at a release rate other than a zero order release profile.

The second pharmaceutically active agent may be present in the second layer portion in amount of from about 2 wt. % to about 99 wt. %, preferably from about 50 wt. % to about 95 wt. %. Also optionally present in the second layer portion are binding agents, plasticizers, and antitacking agents. The binding agent preferably also is a film former capable of binding the pharmaceutical agent of the second layer to the core with good adhesion and a smooth film. The binder should be soluble in water or physiological fluids and should be of sufficiently low viscosity so as not to retard the release of the pharmaceutical agent from the second layer. Preferred binders are low viscosity HPMC (hydroxypropylmethyl cellulose), low viscosity HPC (hydroxypropyl cellulose), Eudragit E polymers (aminoalkyl methacrylate copolymers), Eudragit RD 100 (a mixture of ammonioalkyl methacrylate copolymers and sodium carboxymethylcellulose), PVP K30 (polyvinylpyrrolidone) and the like. Optionally, plasticizers and antitacking agents may be added to the layer portion to improve the quality of the film. Acceptable plasticizers include PG (Propylene Glycol), TEC (triethyl citrate), Polysorbate 80, dibutyl phthalate, etc. Antitacking agent examples include, but are not limited to, talc, magnesium stearate, glyceryl monostearate, titanium dioxide and the like. Additionally, commercially available products such as Opadry®, Opagloss®, and Lustre Clear® and others which are ready made mixes of binder, plasticizer and antitacking agents may be used. If the second pharmaceutically active agent is insoluble, the second layer portion may include one or more solubilizing agents as hereinabove described.

Examples of the second pharmaceutically active agent include, but are not limited to, loratidine, desloratidine, astemizole, norastemizole, ebastine, and other antihistamines. It is of particular benefit to apply an antihistamine to the exterior of the present invention when pseudoephedrine and its salts are to be delivered from the interior of the system of the present invention.

Other examples of combinations of pharmaceutically active agents that may be employed in accordance with the present invention include, but are not limited to, those in the field of Parkinson's Disease treatments, such as carbidopa/levodopa and pergolide; drug combinations to treat AIDS including combinations of non-nucleoside analogues, nucleoside analogues, and reverse transcriptase inhibitors such as AZT and DDC, AZT and DDI, AZT and 3TC; and drug combinations useful in the treatment of cancer, allergies, bacterial or viral infection, especially common cold and flu preparations.

The invention now will be described with respect to the drawing, wherein:

The drawing is a schematic of a cross-section of an embodiment of the system of the present invention.

Referring now to the drawing, a tablet 10 in accordance with the present invention includes an osmotic core portion 12, a layer portion 14 enclosing or surrounding the osmotic core portion 12, and a semipermeable membrane or wall 16 surrounding or enclosing layer portion 14 and osmotic core portion 12. The semipermeable membrane or wall 16 includes a passageway or hole 15 extending from the layer portion 14 through the semipermeable wall 16 to the external environment. Passageway 15 thus aids the passage of the pharmaceutically active agent into the system of the patient.

Osmotic core 12 includes the pharmaceutically active agent in an amount of from about 1 wt. % to about 80 wt. % of the total weight of the osmotic core, preferably from about 15 wt. % to about 70 wt. %, more preferably about 60 wt. %. The pharmaceutically active agent may be selected from those hereinabove described.

Layer portion 14, which surrounds or encloses osmotic core 12, includes the pharmaceutically active agent in an amount of from about 20 wt. % to about 99 wt. % of the total weight of the layer, preferably from about 50 wt. % to about 95 wt. %, and more preferably about 90 wt. %.

When the tablet 10 is administered orally, bodily fluids, such as saliva from the mouth, hydrochloric acid and gastric juices from the stomach, and other digestive juices from the intestines, will travel through the semipermeable wall 16, and contact the pharmaceutically active agent in the layer portion 14, whereby the pharmaceutically active agent begins to exit from tablet 10 through the passageway 15 and into the body. Thus, there is a quick, yet effective and controlled, initial release of the pharmaceutically active agent into the body. Once a portion of the pharmaceutically active agent in layer portion 14 has diffused out of the tablet 10 and into the body, bodily fluids pass through semipermeable wall 16 and contact the pharmaceutically active agent in osmotic core portion 12, whereby the pharmaceutically active agent in osmotic core portion 12 and remaining pharmaceutically active agent in layer portion 14 pass through passageway 15 and into the body. The concentration of the pharmaceutically active agent in the osmotic core portion 12 is less than the concentration of the pharmaceutically active agent in layer portion 14; thus, the pharmaceutically active agent is released more slowly into the body from osmotic core portion 12 than it is from layer portion 14. The combination of osmotic core portion 12, layer portion 14, and semipermeable wall 16 with passageway 15, wherein the concentration of the pharmaceutically active agent is higher in layer portion 14 than in core portion 12, provides for a fast, initial yet effective controlled release of the pharmaceutically active agent into the body without excessive "dose dumping," followed by a slower controlled release of the pharmaceutically active agent. The semipermeable wall 16 also limits the exposure of the pharmaceutically active agent to bodily fluids outside tablet 10 such that the contact of the pharmaceutically active agent with the bodily fluids is such that the pharmaceutically active agent exits through passageway 15 into the digestive and circulatory systems of the patient, but such contact is not to an excessive degree whereby the pharmaceutically active agent is degraded by the bodily fluids. Thus, in effect, the drug delivery from the osmotic tablet 10 approaches or reaches a first order release profile and is other than a zero order release profile.

The releases of the pharmaceutically active agent from layer portion 14 and from osmotic core 12 combine to provide a release profile which approaches or reaches first order and is other than zero order, which is not found in tablets having a semipermeable wall that encloses or surrounds only an osmotic core, or in tablets having a semipermeable wall which encloses or surrounds only an osmotic core portion, and which has a layer of pharmaceutically active agent or drug on the outside of the semipermeable wall.

The invention now will be described with respect to the following examples; however, the scope of the present invention is not intended to be limited thereby.

EXAMPLE 1

Psuedoephedrine Sulfate Granulation Tableting/Coating

An aqueous solution of polyvinylpyrrolidone (PVP), sugar or other binder can be used as the granulating solution. A fluid bed bowl is charged with osmagents (xylitol, maltrin, sodium chloride, etc.). The remaining amount of pseudoephedrine sulfate and other ingredients as required then is added.

The granulating solution is sprayed onto the powder bed with a spray rate of 5–20 g/min, which will produce granules of an adequate size for tableting. (Spray rate will vary with batch size.) Inlet airflow rate and temperature are adjusted to keep powder bed from over-granulating or becoming overly wet. (Typical range 100–250 CMH (cubic meters per hour) and 40–60° C., depending on batch size.)

The granulation is discharged and suitable lubricant, such as magnesium stearate or stearic acid (approximately 0.5–3.0%) is added and blended 2–5 minutes or as necessary in a V-blender.

The blend is discharged from the mixer and tableted on a suitable tablet press. The tablets are coated in a pan coater or a fluid bed dryer with spray rate of 10–40 g/min or higher (depending on batch size) first for the drug layer and 30–60 g/min or higher (depending on batch size) for the second coating of the semi-permeable layer. The drug layer coating solution is prepared by adding about 13% of pseudoephedrine sulfate to ethyl alcohol or other suitable solvent. A binder such as Klucel EF (hydroxypropyl cellulose) is added to the suspension at 1–2%. The semi-permeable coating, applied after the drug layer, is prepared by dissolving about 5% cellulose acetate, NF (National Formulary) in acetone or other suitable solvent, and then adding 1–2% plasticizers such as TEC (triethyl citrate) or PG (propylene glycol) or a mixture thereof.

To obtain the desired release rate, one or more holes may be provided. It may be beneficial for a tablet to include a hole on both sides of the tablet to attain the optimum release rate.

EXAMPLE 2

Pseudoephedrine Sulfate Formulations

The following, shown in Table 1 below, are examples of formulations of the homogeneous composition of the tablet core within the tablet wall of the dosage form of the invention which vary in coating levels of the semipermeable membrane and hole properties. The granulations were made according to the method of example 1 above.

TABLE 1

| Ingredients | A | B |
|---|---|---|
| Pseudoephedrine Sulfate | 63.7 | 63.7 |
| Xylitol CM90 | 14.3 | |
| Maltrin M150 | 19.4 | |
| Magnesium Stearate | 1.0 | 0.5 |
| Stearic Acid | 2.0 | 2.0 |
| NaCl | | 24.2 |
| Myrj 52S | | 5.0 |
| PVP 30 | | 5.0 |
| Total | 100 | 100 |

Xylitol CM 90 is a crystaline milled grade of xylitol, Maltrin M150 is a commercially available grade of maltodextrin, and Myrj 52S is polyoxyl-2-cetyl ether.

Xylitol CM90 is a crystaline milled grade of xylitol, Maltrin M150 is a commercially available grade of maltodextrin, and Myrj 52S is polyoxyl-2-cetyl ether.

EXAMPLE 3

The following formulations, given in Table 2 below, are examples of the first layer portion which is applied to the core portion.

TABLE 2

| Ingredients | A | B |
|---|---|---|
| Pseudoephedrine Sulfate | 15.0 | 13.75 |
| Water | 80.0 | — |
| Ethyl Alcohol | — | 85 |
| Hydroxypropyl Cellulose | — | 1.25 |
| Hydroxypropylmethyl Cellulose E5 | 5.0 | — |
| Total | 100 | 100 |

The disclosures of all patents and publications (including published patent applications) are hereby incorporated by reference to the same extent as if each patent and publication were specifically and individually incorporated by reference.

It is to be understood, however, that the scope of the present invention is not to be limited to the specific embodiments described above. The invention may be practiced other than as particularly described and still be within the scope of the accompanying claims.

What is claimed is:

1. An osmotic system for delivering a pharmaceutically active agent, comprising:
    a core portion, wherein said core portion includes said pharmaceutically active agent at a first concentration;
    a layer portion enclosing and directly adjacent to said core portion, wherein said layer portion includes said pharmaceutically active agent at a second concentration, said second concentration being greater than said first concentration; and
    a semipermeable wall portion enclosing said core portion and said layer portion.

2. The system of claim 1 wherein said pharmaceutically active agent is a protein or peptide.

3. The system of claim 1 wherein said semipermeable wall portion is formed from cellulose acetate.

4. The system of claim 1 wherein said pharmaceutically active agent is present in said portion in an amount of about 60 wt. %.

5. The system of claim 1 wherein said pharmaceutically active agent is present in said layer portion in an amount of about 90 wt. %.

6. The system of claim 1 wherein said pharmaceutically active agent is pseudoephedrine or its salts.

7. An osmotic system for delivering a first pharmaceutically active agent and a second pharmaceutically active agent, comprising:
    a core portion, wherein said core portion includes said first pharmaceutically active agent at a first concentration;
    a first layer portion enclosing and directly adjacent to said core portion, wherein said layer portion includes said first pharmaceutically active agent at a second concentration, said second concentration being greater than said first concentration;
    a semipermeable wall portion enclosing said core portion and said first layer portion; and
    a second layer portion including a second pharmaceutically active agent, said second layer enclosing said semipermeable wall portion.

8. The system of claim 7 wherein said first pharmaceutically active agent is present in said core portion in an amount of about 60 wt. %.

9. The system of claim 7 wherein said first pharmaceutically active agent is present in said first layer portion in an amount of about 90 wt. %.

10. The system of claim 7 wherein said second pharmaceutically active agent is present in said second layer portion in an amount of from about 2 wt. % to about 99 wt. %.

11. The system of claim 10 wherein said second pharmaceutically active agent is present in said second layer portion in an amount of from about 60 wt. % to about 95 wt. %.

12. The osmotic system of claim 1, wherein said pharmaceutically active agent is an antitussive, antihistamine, expectorant or decongestant.

13. The osmotic system of claim 12, wherein said pharmaceutically active agent is chlorpheneramine or its salts, diphenhydramine, or dimenhydramine.

14. The osmotic system of claim 1, wherein said pharmaceutically active agent is cyctosporin, carmustine, carbamazepine, desmopreson, dihydroergotamine, fluorouracil, heparin sodium, ribavirin, sumitriptan succinate, flutamide, naltrexone HCl, terbutaline sulfate, triamterene, terazosin, parazosin, nifedipine, calcitonin, parathyroid hormone, or GLP-1.

15. The osmotic system of claim 7, wherein said first pharmaceutically active agent is an antitussive, antihistamine, expectorant or decongestant.

16. The osmotic system of claim 15, wherein said first pharmaceutically active agent is chlorpheneramine or its salts, diphenhydramine, or dimenhydramine.

17. The osmotic system of claim 15, wherein said first pharmaceutically active agent is pseudoephedrine or its salts.

18. The osmotic system of claim 7, wherein said first pharmaceutically active agent is cyclosporin, carmustine, carbamazepine, desmopreson, dihydroergotamine, fluorouracil, heparin sodium, ribavirin, sumitriptan succinate, flutamide, naltrexone HCl, terbutaline sulfate, triamterene, calcitonin, insulin, parathyroid hormone, or GLP-1.

19. The osmotic system of claim 15, wherein said second pharmaceutically active agent is loratidine, desloratidine, astemizole, norastemizole or ebastine.

20. The osmotic system of claim 7, wherein said first pharmaceutically active agent is pseudoephedrine or its salts, and said second pharmaceutically active agent is loratidine.

* * * * *